(12) United States Patent
Smith et al.

(10) Patent No.: US 11,420,073 B2
(45) Date of Patent: Aug. 23, 2022

(54) METHOD OF TREATMENT OF EYELID LAXITY

(71) Applicant: Queensland Eye Institute Foundation, South Brisbane (AU)

(72) Inventors: Tai Mountford Smith, Kalinga (AU); Brendan Gerard Cronin, Clayfield (AU); Shuko Suzuki, Ormeau (AU); Traian Vasile Chirila, Robertson (AU)

(73) Assignee: Queensland Eye Institute Foundation, South Brisbane (AU)

( * ) Notice: Subject to any disclaimer, the term of this patent is extended or adjusted under 35 U.S.C. 154(b) by 96 days.

(21) Appl. No.: 17/070,878

(22) Filed: Oct. 14, 2020

(65) Prior Publication Data

US 2021/0023388 A1    Jan. 28, 2021

Related U.S. Application Data

(63) Continuation of application No. 15/900,583, filed on Feb. 20, 2018, now abandoned.

(30) Foreign Application Priority Data

Feb. 21, 2017    (AU) ................................ 2017900561

(51) Int. Cl.
*A61N 5/06* (2006.01)
*A61N 5/10* (2006.01)

(52) U.S. Cl.
CPC ........... *A61N 5/0616* (2013.01); *A61N 5/062* (2013.01); *A61N 5/1017* (2013.01); *A61N 2005/0661* (2013.01)

(58) Field of Classification Search
CPC ...................................................... A61N 5/06
See application file for complete search history.

(56) References Cited

U.S. PATENT DOCUMENTS

| 6,176,854 B1 * | 1/2001 | Cone .................... A61B 18/203 606/15 |
|---|---|---|
| 2011/0118654 A1 | 5/2011 | Muller et al. |
| 2014/0194957 A1 | 7/2014 | Rubinfeld et al. |
| 2015/0088231 A1 * | 3/2015 | Rubinfeld ............. A61F 9/0079 607/90 |
| 2018/0236261 A1 | 8/2018 | Smith et al. |

OTHER PUBLICATIONS

Arrocker-Mettinger et al.; Floppy eyelid syndrome: Investigations by light and electron microscopies; Klin. Mbl. Augenheilk; 188; pp. 596-598; (Wth English Abstract); (year of pub. sufficiently earlier than effective US filing date and any foreign priority date) 1986.
Benjamin et al.; Biology of fibrocartilage cells; International review of cytology; 233; pp. 1-45; Jan. 1, 2004.

(Continued)

*Primary Examiner* — Lynsey C Eiseman
(74) *Attorney, Agent, or Firm* — Shay Glenn LLP

(57) ABSTRACT

A method of treating eyelid laxity in a subject comprising exposing a tarsal plate of an eye, and applying to at least part of the exposed tarsal plate a photosensitizer that initiates crosslinking in response to photo-activating radiation; and irradiating the exposed tarsal plate with photo-activating radiation to initiate crosslinking in the tarsal plate tissue.

12 Claims, 12 Drawing Sheets

(56) References Cited

OTHER PUBLICATIONS

Boileau et al.; Diseases of the eye; Sheep and Goat Medicine, 2nd Edn, D.G. Pugh, A.N. Baird (Eds), Elsevier, Amsterdam; Chapter 14; pp. 406-410; Sep. 8, 2011.

Ezra et al.; Changes in tarsal plate fibrillar collagens and elastic fiber phenotype in floppy eyelid syndrome; Clinical and Experimental Opthalmology; 39(6); pp. 564-571; Aug. 1, 2011.

Ezra et al.; Floppy eyelid syndrome: stretching the limits; Survey of Ophthalmology; 55(1); pp. 35-46; Jan. 1, 2010.

Ezra et al.; Surgical anatomy of the upper eyelid: old controversies, new concepts; Expert Review of Ophthalmology; 4(1); pp. 47-57; Feb. 1, 2009.

Fowler et al.; Floppy eyelid syndrome as a subject of lax eyelid conditions: relationships and clinical relevance (an ASOPRS thesis); Ophthalmic Plastic and Reconstructive Surgery; 26(3); pp. 195-204; May 1, 2010.

Goldberg et al.; Floppy eyelid syndrome and blefarochalasis; Am. J. Ophthalmol.; 102; pp. 376-381; Sep. 15, 1986.

Milz et al.; An immunohistochemical study of the extracellular matrix of the tarsal plate in the upper lid in human beings; Journal of Anatomy; 206(1); pp. 37-45; Jan. 1, 2005.

Netland et al.; Histopathologic features of the floppy eyelid syndrome: Involvement of tarsal elastin; Opthalmology; 101(1); pp. 174-181; Jan. 1, 1994.

Samuelson; Ophthalmic structures; Essentials of Veterinary Opthalmology, 3rd Edn, K.N. Gelatt (Ed.), Wiley, Oxford, UK; Chapter 2; pp. 12-39; (year of pub. sufficiently earlier than effective US filing date and any foreign priority date) 2014.

Schlotzer-Schrehardt et al.; The pathogenesis of floppy eyelid syndrome: involvement of matrix metalloproteinases in elastic fiber degradation; Opthalmology; 112(4); pp. 694-704; Apr. 1, 2005.

\* cited by examiner

METHOD OF TREATMENT OF EYELID LAXITY

CROSS REFERENCE TO RELATED APPLICATIONS

This application is a continuation of U.S. patent application Ser. No. 15/900,583, filed Feb. 20, 2018, titled "METHOD OF TREATMENT OF EYELID LAXITY," now U.S. Patent Application Publication No. 2018/0236261, which claims priority to Australian Provisional Application No. 2017900561 entitled "METHOD OF TREATMENT" filed on Feb. 21, 2017, the entire content of which is incorporated herein by reference.

FIELD

The methods, apparatuses and compositions herein relate generally to a method of treatment of eyelid laxity, and in particular to a method comprising exposure of the tarsal plate followed by irradiation in the presence of a photosensitizer to enhance the rigidity or strength of the tarsal plate and inhibit the progression of the disorder.

BACKGROUND

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavor to which this specification relates.

The condition known as eyelid laxity (or lax eyelid), also known as floppy eyelid syndrome (FES), is regarded as a subset of the conditions generated by the laxity of the eyelid [see A. M. Fowler, J. J. Dutton: "Floppy eyelid syndrome as a subset of lax eyelid conditions: Relationships and clinical relevance (an ASOPRS thesis)", *Ophthal. Plast. Reconstr. Surg.*, 26 (2010) 195-204]. Eyelid laxity can be defined as an acquired hyperelasticity disorder where the inherent rigidity of the lids is lost. It can affect both upper and lower eyelids. Due to corneal complications and associations with other eyelid disorders, a floppy eyelid can lead to blindness. Eyelid laxity is commonly associated with other conditions including obesity, cardiovascular disease, obstructive sleep apnea, and eye rubbing.

The main clinical feature of a floppy eyelid is the extreme laxity of the upper or lower tarsus (or tarsal plate), which becomes pliant and rubbery. In normal conditions, the upper or lower tarsal plate is a specialized dense fibrous tissue that is able to display significant rigidity and provide structural integrity, shape and firmness to the entire eyelid. Tarsal plate tissue can be regarded as a unique tissue with transient character possessing features common to both cartilage and fibers [see a description of fibrocartilage tissues in M. Benjamin, J. R. Ralphs: "Biology of fibrocartilage cells", *Int. Rev. Cytol.*, 233 (2004) 1-45]. The tarsal tissue consists mainly of fibrillar collagens type I, III and, to a lesser extent, type VI, as well as elastic networks of fibrillin and elastin fibers [see: S. Milz, J. Neufang, I. Higashiyama, R. Putz, M. Benjamin: "An immunohistochemical study of the extracellular matrix of the tarsal plate in the upper lid in human beings", *J. Anat.*, 206 (2005) 37-45; D. G. Ezra, M. Beaconsfield, R. Collin: "Surgical anatomy of the upper eyelid: old controversies, new concepts", *Expert Rev. Ophthalmol.*, 4 (2009) 47-57]. In the tarsal plates of the lax eyelids, the collagen expression, structure and distribution remains the same as in normal tarsus, as was reported for instance in: R. Goldberg, S. Seiff, J. McFarland, K. Simons, N. Shorr: "Floppy eyelid syndrome and blefarochalasis", *Am. J. Ophthalmol.*, 102 (1986) 376-381; and E. Arrocker-Mettinger, R. Haddad, K. Konrad, F. J. Steinkogler: "Floppy eyelid syndrome: Investigations by light and electron microscopies" (Ger.), *Klin. Mbl. Augenheilk.*, 188 (1986) 596-598. However, the decrease in the amount of elastin and mature elastic fibers observed histopathologically in the tarsal plate of a lax eyelid [as reported for instance in: P. A. Netland, S. P. Sugrue, D. M. Albert, J. W. Shore: "Histopathologic features of the floppy eyelid syndrome. Involvement of tarsal elastin", *Ophthalmology*, 101 (1994) 174-181; U. Schlötzer-Schrehardt, M. Stojkovic, C. Hofmann-Rummelt, C. Cursiefen, F. E. Kruse, L. M. Holbach: "The pathogenesis of floppy eyelid syndrome. Involvement of matrix metalloproteinases in elastic fiber degradation", *Ophthalmology*, 112 (2005) 694-704] is not consistent with an enhanced elasticity and reduced mechanical strength that have been evidenced clinically. A more recent study [D. G. Ezra, J. S. Ellis, C. Gaughan, M. Beaconsfield, R. Collin, C. Bunce, M. Bailly, P. Luthert: "Changes in tarsal plate fibrillar collagens and elastic fiber phenotype in floppy eyelid syndrome", *Clin. Exp. Ophthalmol.*, 39 (2011) 564-571] has demonstrated that instead of a reduction of elastic fibers in the tarsal plates belonging to lax eyelids, the main process consists rather of a change in the phenotype of these fibers. The same study also confirmed that the expression and periodicity of the main fibrillar collagens remain normal.

Current treatment methods for eyelid laxity include nocturnal lid shielding, taping or lubrication. These treatment methods generally only provide temporary benefit. Surgical methods may be used to tighten the lid. These surgical methods include full-thickness wedge excision; lateral tarsal strip; lateral canthal tendon plication; or lateral tarsorrhaphy (D. G. Ezra, M. Beaconsfield, R. Collin: "Floppy eyelid syndrome: Stretching the limits", *Surv. Ophthalmol.*, 55 (2010) 35-46).

These surgical horizontal tightening procedures usually only provide temporary benefit as the eyelid tissue continues to stretch with time and the eyelid laxity returns. Furthermore, these surgical procedures are usually performed under general anesthesia. This is a particular problem as many patients with floppy eye syndrome are commonly also afflicted by cardiovascular disease, obesity and sleep apnea: conditions that require particular considerations with respect to administration of general anesthesia.

There is a need for improved methods for treating or inhibiting the progression of eyelid laxity that overcome one or more drawbacks of the present therapies.

SUMMARY

The methods, compositions and apparatuses herein are predicated in part on the surprising discovery that exposure of a tarsal plate to radiation in the presence of a photosensitizer initiates crosslinking within the tissue, and particularly crosslinking of collagen in the tarsal plate tissue. This crosslinking has been found to improve or restore strength or rigidity to the tarsal plate resulting in arresting or slowing the progression of eyelid laxity.

Accordingly, in one aspect the methods herein advantageously provide a method of treating eyelid laxity in a subject comprising:

exposing a tarsal plate of an eye;
applying to at least part of the exposed tarsal plate a photosensitizer that initiates crosslinking in response to photo-activating radiation; and
irradiating the exposed tarsal plate with photo-activating radiation to initiate crosslinking activity in the tarsal plate tissue.

The method suitably further comprises making an incision to expose the tarsal plate and subsequent closure of the incision after irradiation with the photo-activating radiation.

The inventors have discovered that it is desirable that the photosensitizer is in solubilized form, suitably in the form of an aqueous composition. The method may advantageously include delivery of $O_2$ at the site of crosslinking.

The methods herein may be applied to one or both eyes of a subject, individually, simultaneously or sequentially; or to the upper and/or lower tarsal plates of an eye, individually, simultaneously or sequentially. A method may be performed simultaneously or sequentially in combination with an additional surgical tightening procedure.

In another aspect, there is provided a system for crosslinking tarsal plate tissue comprising:
an applicator that applies or delivers a photosensitizer to an exposed tarsal plate of an eye; and
a radiation source that provides photo-activating radiation to the tarsal plate with a beam profile of greater than 12 mm at a distance of about 10 mm from a surface of the tarsal plate.

In another aspect, there is provided a kit or commercial package for crosslinking tarsal plate tissue comprising:
an applicator that applies or delivers a photosensitizer to an exposed tarsal plate of an eye; and
a radiation source for providing photo-activating radiation to the tarsal plate;
together with instructions to treat eyelid laxity or crosslink a tarsal plate or tarsal plate tissue.

The system, kit or commercial package may further include a means of delivering $O_2$ to the site of crosslinking.

In a yet further aspect, there is advantageously provided herein a photosensitizer that initiates crosslinking in response to photo-activating radiation for use in treatment or prevention of eyelid laxity.

In a yet further aspect, the methods herein advantageously provide use of a photosensitizer that initiates crosslinking in response to photo-activating radiation for crosslinking of tarsal plate tissue.

In another aspect, there is provided the use of a photosensitizer that initiates crosslinking in response to photo-activating radiation for the manufacture of a medicament for treatment of eyelid laxity.

In another aspect, there is provided a use of a photosensitizer that initiates crosslinking in response to photo-activating radiation for inhibiting the progression or development of eyelid laxity in a subject.

The inventors have found it desirable to use riboflavin or a pharmaceutically acceptable salt, derivative and/or solvate thereof as a photosensitizer in combination with UV-A photo-activating radiation. In preferred embodiments the riboflavin is in a water soluble form, for example a water soluble salt, derivative and/or solvate thereof.

In a further aspect, there is advantageously provided a pharmaceutical composition comprising a photosensitizer, for example riboflavin or a pharmaceutically acceptable salt, derivative or solvate thereof, for use in combination with photo-activating radiation for treatment or prevention of eyelid laxity.

In another aspect, the apparatuses herein also provide a kit or commercial package comprising a pharmaceutical composition comprising a photosensitizer that initiates crosslinking in response to photo-activating radiation; together with instructions for use in combination with photo-activating radiation to treat eyelid laxity, or to effect crosslinking in a tarsal plate or tarsal plate tissue. In some embodiments the photosensitizer is riboflavin or a pharmaceutically acceptable salt, derivative or solvate thereof. In some embodiments the pharmaceutical composition is an aqueous composition. In some embodiments the photosensitizer is in solubilized form.

DETAILED DESCRIPTION

1. Definitions

Figure 1A:
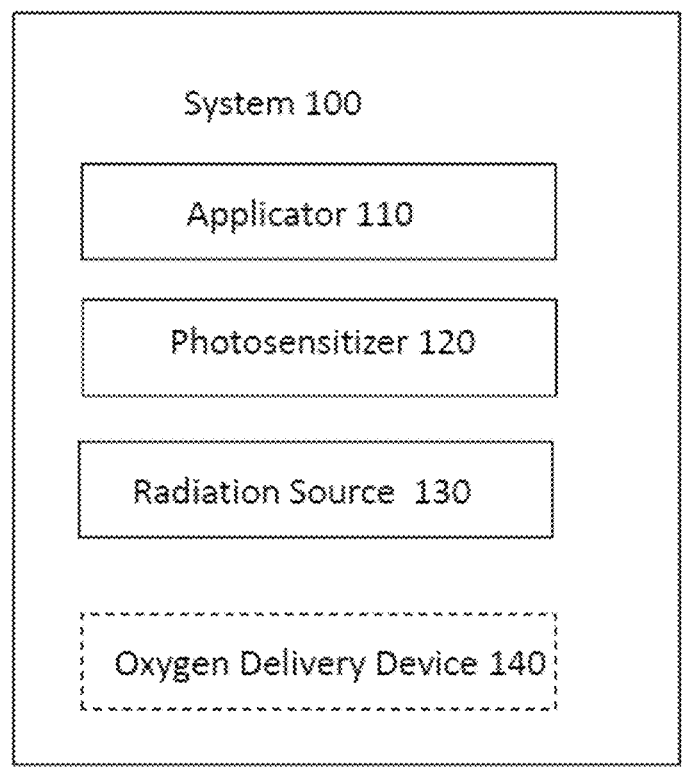
FIG. 1A is a schematic representation of a system according to some embodiments of the disclosure.

Unless defined otherwise, all technical and scientific terms used herein have the same meaning as commonly understood by those of ordinary skill in the art to which the methods, compositions and apparatuses herein belong. Although any methods and materials similar or equivalent to those described herein can be used in the practice or testing of the present methods, compositions and apparatuses, preferred methods and materials are described. For the purposes of the methods, compositions and apparatuses herein, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much 15, 14, 13, 12, 11, 10, 9, 8, 7, 6, 5, 4, 3, 2 or 1% to a reference quantity, level, value, number, frequency, percentage, dimension, size, amount, weight or length.

As used herein, the term "and/or" refers to and encompasses any and all possible combinations of one or more of the associated listed items, as well as the lack of combinations when interpreted in the alternative (or).

The phrase "aqueous carrier" is used herein to refer to a liquid aqueous diluent, wherein the aqueous carrier includes, but is not limited to, water, saline, aqueous buffer and aqueous solutions comprising water soluble or water miscible additives such as glucose or glycerol. The aqueous carrier may also be in the form of an oil-in-water emulsion.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. Thus, the use of the term "comprising" and the like indicates that the listed integers are required or mandatory, but that other integers are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the terms "condition" or "disease" refers to an abnormality in the physical state of the body as a whole or one of its parts.

As used herein, the term "salts", "derivative" and "solvate" include any pharmaceutically acceptable salt, derivative, or solvate or any other compound which, upon administration to the recipient, is capable of providing (directly or indirectly) a desired photosensitizer. Suitable pharmaceutically acceptable derivatives include esters, such as phosphate esters. Suitable pharmaceutically acceptable salts include salts of pharmaceutically acceptable inorganic acids such as hydrochloric, sulfuric, phosphoric, nitric, carbonic, boric, sulfamic and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acids. Base salts include, but are not limited to, those formed with pharmaceutically acceptable cations, such as sodium, potassium, lithium, calcium, magnesium, ammonium and alkylammonium, particularly sodium. Also, basic nitrogen-containing groups may be quaternized with such agents as lower alkyl halides, such as methyl, ethyl, propyl and butyl chlorides, bromides and iodides; dialkyl sulfates such as dimethyl and diethyl sulfate; and others. Pharmacologically acceptable solvates are known in the art, and include hydrates and alcoholates. Suitably, pharmaceutically acceptable solvates include hydrates, for example monohydrates, dihydrates and trihydrates. The skilled person will understand that a photosensitizer may be in the form of a pharmaceutically acceptable salt, and/or a solvate and/or a derivative, for example riboflavin 5'-phosphate monosodium salt dihydrate and the like. The preparation of salts, derivatives and solvates can be carried out by methods well known in the art.

As used herein, the phrase "solubilized form" refers to a form where a compound, such as a photosensitizer, is dissolved in a liquid such that a solution comprising a uniform distribution of the compound is obtained which is substantially free of solid compound. In some embodiments, the liquid is an aqueous carrier as described herein.

As used herein "water soluble form" refers to a chemical and/or physical form of a compound, such as a photosensitizer, where the compound or a salt and/or derivative and/or solvate and/or polymorph thereof has sufficient solubility in water at ambient temperature to achieve a concentration of from 0.1% to 20% w/v, 0.1% to 10% w/v, 0.1% to 5% w/v, 0.1% to 3%, 0.1% to 2.5%, 0.1% to 1%, 0.1% to 0.5%, or 0.1% to 0.25%. Solubility can be determined using methods well known in the art.

The term "subject" or "individual" as used herein refers to a vertebrate subject, particularly a mammalian subject, for whom therapy or prophylaxis is desired. Suitable subjects include, but are not limited to, primates; livestock animals such as sheep, cows, horses, deer, donkeys and pigs; laboratory test animals such as rabbits, mice, rats, guinea pigs and hamsters; companion animals such as cats and dogs; and captive wild animals such as foxes, deer and dingoes. In particular embodiments, the subject is a human. However, it will be understood that the aforementioned terms do not imply that symptoms are present.

The term "eyelid laxity" or "floppy eyelid syndrome" when used herein refers to conditions where an acquired hyperelasticity disorder in an eyelid has resulted in the inherent rigidity of the eyelid being lost.

When used herein, the term "photosensitizer" refers to a molecule that, on irradiation by photo-activating irradiation, produces a chemical change in another molecule through a photochemical process. Examples of "another molecule" include, for example, a crosslinker or crosslinking agent such as $O_2$. A photosensitizer may convert $O_2$ molecules from the normal $O_2$ triplet state to a more energetic singlet state that can initiate crosslinking, for example in tissue molecules or macromolecules. Further examples of "another molecule" include tissue molecules or macromolecules, including collagen macromolecules. A photosensitizer, after exposure to radiation and transition to a more energetic state, may also produce a chemical change in collagen and/or other tissue molecules and initiate or generate crosslinking in the tissue. The skilled person will appreciate that optimum results will be achieved when the selected photosensitizer absorbs radiation at a wavelength of the photo-activating radiation. The absorption wavelength(s) of a photosensitizer can be determined by Ultraviolet/Visible (UV/VIS) Spectrophotometry using a commercially available UV/VIS spectrophotometer in accordance with well known procedures. A photosensitizer will preferably be pharmaceutically acceptable, non-irritant and non-toxic.

When used herein, the term "crosslinker" or "crosslinking agent" refers to a chemical moiety that can chemically join two or more molecules, for example by covalent bonding or ionic bonding, preferably by covalent bonding. An example of a crosslinking agent is $O_2$ which acts as a crosslinking agent when in the form of its high energy singlet state. A crosslinker or crosslinking agent will preferably be pharmaceutically acceptable. A molecule may be a macromolecule. Preferably a crosslinker or crosslinking agent will be substantially non-irritant and non-toxic.

The term "photo-activating radiation" when used herein refers to radiation that can activate a photosensitizer to produce a chemical change in another molecule. Suitably the photosensitizer absorbs radiation at a wavelength of the photo-activating radiation. In some embodiments the radiation is UV-A radiation.

The terms "treat", "treating" or "treatment" as used herein cover the treatment of eyelid laxity, and includes: inhibiting the disease or condition, i.e., arresting its development; relieving the disease or condition, i.e., causing regression of the disease or condition; or relieving the symptoms resulting from the disease or condition, i.e., relieving pain or inflammation without addressing the underlying disease or condition.

Each embodiment described herein is to be applied mutatis mutandis to each and every embodiment unless specifically stated otherwise.

2. Methods

The present methods are based, in part, on the identification that irradiation of tarsal plate tissue in the presence of a photosensitizer can significantly enhance the mechanical rigidity and strength of the tarsal plate. Thus, the inventors conceived that treatment of eyelid laxity or inhibition of the development of eyelid laxity may be achieved by irradiating an exposed tarsal plate with photo-activating radiation in the presence of a photosensitizer.

These surprising findings have enabled the development of a method of treating eyelid laxity comprising subjecting an exposed tarsal plate to photo-activating radiation in the presence of a photosensitizer to crosslink tarsal tissue and thus strengthen the tarsal plate. This leads to slowing or arresting of the progression of eyelid laxity. This provides a simple and effective procedure for treatment of eyelid laxity. The method addresses a major drawback of known surgical interventions where the benefit is temporary as the eyelid continues to stretch and the laxity returns. The method impacts on the underlying pathology in that it prevents or arrests tarsal stretching. Furthermore, the method can provide sustained benefit from surgery when combined with additional tightening procedures, such as surgical tightening procedures including full-thickness wedge excision; lateral tarsal strip; lateral canthal tendon plication; or lateral tarsorrhaphy. The method can also be used as a prophylactic treatment in at-risk patients before the symptoms arise. Furthermore, the method does not significantly alter the macroscopic eyelid anatomy, so it can be performed prior to, in combination with, or subsequent to other eyelid operations. Another advantage of the method is that it can be performed under local anesthesia, making it more acceptable to patient affected by the often associated conditions of cardiovascular disease, obesity and sleep apnea.

Without being bound by theory or mode of operation, it is believed that the photosensitizer initiates crosslinking within the tarsal plate tissue, particularly crosslinking of collagen macromolecules, when exposed to photo-activating radiation. This results in increased rigidity and strength of the tarsal plate. It is believed that the photosensitizer absorbs radiation and is raised to an energetically excited state, which further initiates reactions within the tarsal plate tissue, particularly in constitutive collagen (Type I reactions) and with $O_2$ (Type II reactions). Both types of reaction are thought to be able to generate covalent crosslinkages between the macromolecules in the tarsal tissue, particularly crosslinkages between collagen macromolecules.

It is believed that the collagen expression, structure and distribution remains the same in the tarsal plates of the lax eyelids as that found in the normal tarsus. However, the decrease in the amount of elastin and mature elastic fibers observed histopathologically in the tarsal plate of a lax eyelid is not consistent with an enhanced elasticity and reduced mechanical strength that is evidenced clinically. Instead of a reduction of elastic fibers in the tarsal plates of lax eyelids, the main process appears to involve a change in the phenotype of these fibers. The expression and periodicity of the main fibrillar collagens remain normal. Since an unaltered integration of the elastic fiber networks (imparting compliance and elasticity) with the collagen fibers (imparting tensile strength and rigidity) is critical for ensuring and maintaining the normal mechanical properties of the tarsal plate, it is believed that the stiffening of the collagen fibrils in the tarsal plate of a lax eyelid can compensate for the loss of strength and restore the rigidity of the entire plate, leading to the arrest or slowing of eyelid laxity.

Accordingly, in view of the surprising finding that irradiation of tarsal plate tissue in the presence of a photosensitizer can significantly enhance the mechanical rigidity and strength of the tarsal plate, the methods herein advantageously provides a method of treating eyelid laxity in an individual comprising the steps of:

exposing a tarsal plate of an eye;

applying to at least part of the exposed tarsal plate a photosensitizer that generates crosslinking in the tarsal plate tissue in response to photo-activating radiation; and irradiating the exposed tarsal plate with photo-activating radiation to initiate crosslinking in the tarsal plate tissue.

Suitably the methods may be applied to a tarsal plate of an upper eyelid, a lower eyelid, or to both eyelids, subsequently or simultaneously. A method may be applied to eyelids of one or both eyes of a subject, individually, subsequently or simultaneously.

The skilled person, such as an oculoplastic surgeon, will be familiar with methods and procedures for exposing a tarsal plate of an eye, particularly the anterior aspect of the tarsal plate. Suitably the tarsal plate may be exposed by making an incision line horizontally within the eyelid crease (for an upper eyelid), or approximately 3 to 5 mm, for example 4 mm, from the margin in the lower eyelid. The incision is then deepened through the underlying orbicularis oculi muscle down to the orbital septum and creating a pretarsal pocket in the central eyelid area by extending medially and laterally using, for example, a hot temperature cautery instrument, to expose the anterior aspect of the tarsal plate. Suitably the area of the tarsal plate exposed is an area between 25 mm by 10 mm and 15 mm by 5 mm, for example approximately 20 mm by 8 mm, on the upper eyelid; or an area between 25 mm by 6 mm and 15 mm by 2 mm, for example 20 mm by 3 mm, on the lower eyelid.

A photosensitizer is suitably pharmaceutically acceptable, substantially non-toxic and substantially non-irritant. The skilled person will readily understand that different photosensitizers will absorb photosensitizing radiation of specific wavelengths according to the chemical structure of the chromophore, and will be able to match the photosensitizer to the appropriate wavelength of photosensitizing radiation. In some embodiments the photosensitizer absorbs radiation in the ultraviolet region of the electromagnetic spectrum, preferably long wavelength ultraviolet radiation (UV-A radiation, wavelength from 320 to 400 nm). In some other embodiments, the photosensitizer absorbs radiation at a wavelength of 495-570 nm (green light). Preferably the photosensitizer is pharmaceutically acceptable, non-toxic and non-irritant. Preferably the photosensitizer has regulatory approval for food and/or drug use. In some embodiments the photosensitizer may comprise one or more chemical entities. In some embodiments there may be a single photosensitizer molecule type present.

In some embodiments the photosensitizer comprises riboflavin or a pharmaceutically acceptable salt, derivative or solvate thereof. Riboflavin is also known as vitamin $B_2$, and has the IUPAC name 7,8-dimethyl-10-[(2S,3S,4R)-2,3,4,5-tetrahydroxypentyl]benzo[g]pteridine-2,4-dione. Preferably riboflavin is in a water soluble form, for example as a water soluble derivative, salt or solvate, such as an alkali metal salt, of riboflavin 5'-phosphate. Preferably the riboflavin derivative, solvate or salt is non-toxic and non-irritant. In some embodiments the photosensitizer comprises a sodium salt of riboflavin 5'-phosphate or a pharmaceutically acceptable solvate thereof, such as riboflavin 5'-phosphate monosodium salt. Preferably a solvate is a hydrate.

In some embodiments the photosensitizer is rose Bengal (4,5,6,7-tetrachloro-2',4',5',7'-tetraiodofluorescein disodium salt). Preferably rose Bengal is used in conjunction with irradiation by green light, i.e. radiation wavelength 495-470 nm.

In some embodiments the photosensitizer is selected from lucigenin, acridine orange, Quantacure QTX, Lissamine green B, fluorescein, Brilliant blue G, triamcinolone, or trypan blue. In some embodiments the photosensitizer is selected from lucigenin, acridine orange, and Quantacure QTX (2-hydroxy-3-(3,4-dimethyl-9-oxo-9H-thioxanthen-2-yloxy)-N,N,N-trimethyl-1-propanaminium chloride) and the irradiation has a wavelength greater than 300 nm (UV-A/visible).

In some embodiments, the photosensitizer is applied to at least part of the exposed tarsal plate. Suitably the photosensitizer is applied to at least 25%, at least 50%, at least 75%, at least 80%, or at least 90% of the surface of the exposed tarsal plate. Preferably the photosensitizer is applied to substantially the entire surface of the exposed tarsal plate.

In some embodiments the photosensitizer is in solubilized form. Preferably the sensitizer is water soluble. Preferably the sensitizer is in aqueous solution. In preferred embodiments, the photosensitizer is formulated in an aqueous carrier. For example, the aqueous carrier may be selected from, but is not limited to, saline, water, aqueous buffer, an aqueous solution comprising water and a miscible solvent, and combinations thereof. In some embodiments, the aqueous carrier is saline. In preferred embodiments the photosensitizer and aqueous carrier form a sterile solution.

In some embodiments, the photosensitizer is formulated as an aqueous formulation, for example an aqueous solution, an aqueous gel, or an oil in water emulsion, preferably as an aqueous solution. In some embodiments the photosensitizer is present in an amount of 0.1 to 20% w/v. Suitable water soluble photosensitizers are readily available from commercial sources, for example riboflavin 5'-phosphate sodium salt, riboflavin 5'-phosphate sodium salt hydrate and riboflavin 5'-phosphate sodium salt dihydrate are available from Sigma Aldrich Co. LLC. Photosensitizers formulated as a solution are commercially available, for example ParaCel™ (Avedro, Inc, Waltham, Mass., USA) is a commercially available aqueous solution comprising 0.25% riboflavin in the form of riboflavin 5'-phosphate sodium salt, and VibeX Rapid™ (Avedro, Inc) is a commercially available solution comprising 0.1% riboflavin 5'-phosphate sodium salt. In some embodiments the photosensitizer is commercially available as a sterile formulation in a dispenser, for example as a sterile aqueous sodium riboflavin 5'-phosphate solution packaged in a syringe, ampoule, vial or dropper, for example a single use syringe.

The skilled person will understand that the amount of photosensitizer required will depend on the identity of the photosensitizer. In some embodiments the amount of photosensitizer applied to the exposed tarsal plate is from 1 to 5 mL of a solution comprising from 0.1 to 0.5% w/v of photosensitizer, suitably 0.1 to 0.25% w/v. In some embodiments the amount of riboflavin applied to an exposed tarsal plate is 1.8 mL of 0.25% riboflavin (as riboflavin 5'-phosphate) in aqueous carrier; or 2 mL of 0.22% riboflavin (as riboflavin 5'-phosphate) in aqueous carrier; or 3 mL of 0.146% riboflavin (as riboflavin 5'-phosphate) in aqueous carrier or 2 mL of 0.1% riboflavin (as riboflavin 5'-phosphate) in aqueous carrier.

The photosensitizer is applied to the exposed tarsal plate using any suitable means known to the skilled person. In some embodiments the photosensitizer is applied using an applicator. In some embodiments the photosensitiser is applied dissolved in an aqueous carrier, preferably as an aqueous solution. In some embodiments, the photosensitizer is instilled directly onto the surface of the exposed tarsal plate. In some embodiments the photosensitizer is instilled onto the tarsal plate or pretarsal pocket using, a suitable applicator such as a syringe, pipette or dropper. In some embodiments, a pretarsal pocket is formed surgically and the photosensitiser solution is instilled into the pretarsal pocket. In some embodiments, excess photosensitizer is removed from the tarsal plate or pretarsal pocket prior to irradiation. In some embodiments excess photosensitizer solution is removed from the tarsal plate using absorbent material, such as surgical sponge. In some embodiments, photosensitizer solution is first absorbed onto an absorbent material, preferably a disposable textile pad, for example a surgical sponge or neurosurgical patty, prior to application to the exposed tarsal plate or insertion into the tarsal pocket. In some embodiments the photosensitizer is applied to substantially the entire exposed surface of the tarsal plate.

In some embodiments the photosensitizer, preferably in the form of an aqueous solution, is allowed to remain in contact with the exposed tarsal plate for a period of from 6 to 60 minutes, for example 6 to 30 minutes, 30 to 60 minutes, 10 to 30 minutes, 10 to 40 minutes, 6 to 15 minutes, 6 to 20 minutes or 10 to 20 minutes. The exact timing will depend on the amount and concentration of the photosensitizer, and can be easily determined by the skilled person based on the concentration of the photosensitizer solution. In some embodiments the photosensitizer instilled in the pretarsal pocket is 0.1% riboflavin (as riboflavin 5'-phosphate, sodium salt) in aqueous solution which is allowed to contact the tarsal plate for approximately 30 minutes. In some embodiments the photosensitizer instilled in the pretarsal pocket is 0.25% riboflavin (as riboflavin 5'-phosphate, sodium salt) in aqueous solution which is allowed to contact the tarsal plate for approximately 30 minutes.

After the photosensitizer has contacted the tarsal plate for the required length of time, the absorbent material, or excess solution, is removed and the exposed tarsal tissue is exposed to radiation of appropriate wavelength for the photosensitizer used. In some embodiments the photosensitizer is a sodium salt of riboflavin 5'-phosphate and the radiation is UV-A radiation of wavelength of about 320 nm to about 400 nm. In some embodiments the UV-A radiation wavelength is approximately 365 nm.

Treatment of the tarsal plate with photo-activating radiation may be simultaneous and/or subsequent to treatment with a photosensitizer. In some embodiments additional photosensitizer may be applied to the tarsal plate during irradiation.

The skilled person will understand that the irradiation time necessary to induce sufficient crosslinking in the tarsal plate tissue will be dependent on several factors including the irradiance intensity delivered by the radiation source ($mW/cm^2$), and the beam width. Preferably, use of an irradiance of about 3 $mW/cm^2$ up to about 150 $mW/cm^2$ is envisaged. It will also be appreciated that the radiant exposure should not be detrimental to the health of the tissue. A radiant exposure, or fluence, of about 4 to about 27 $J/cm^2$ is considered appropriate. In some embodiments, the radiant exposure of the tarsal tissue, or fluence, is from about 5 to about 8 $J/cm^2$. In some embodiments, the fluence is about 27 $J/cm^2$. The skilled person will be able to determine the duration of the exposure required based on the power of the radiation.

Suitably, the tarsal tissue is exposed to UV-A radiation (320 nm to 400 nm, for example 365 nm) at an irradiance of about 3 to about 6 $mW/cm^2$, for example about 3 $mW/cm^2$ or about 6 $mW/cm^2$. In some embodiments, irradiation of the photosensitizer treated tarsal plate with UV-A radiation is maintained for a duration between about 6 minutes and about one hour, for example 6 to 40 minutes, 6 to 30 minutes, 6 to 20 minutes or 6 to 10 minutes.

In some embodiments, the irradiation may be carried out at high irradiance, for example at 30-45 $mW/cm^2$ for 1 to 4 minutes, for example 2 to 3 minutes. In some embodiments the radiant exposure, or fluence, is from about 5 to 8 $J/cm^2$, for example from about 5.4 to 7.2 $J/cm^2$.

The skilled person will appreciate that there will be an upper limit to the amount of irradiation that is considered useful. It is considered that irradiation levels of up to and including 150 $mW/cm^2$, for example 150 $mW/cm^2$, may be used safely. Irradiation at a level of 150 $mW/cm^2$ should be carried out for up to 4 minutes, or up to 3 minutes; for example 1 to 4 minutes, 1 to 3 minutes, 2 to 3 minutes, 1 to 2 minutes, or approximately 1 minute. Irradiances exceeding 150 $mW/cm^2$ are considered to be less effective in improving the stiffness or strength of tarsal tissue. This is thought to be due to the presence of competing photodegradative processes which may prevail over the beneficial crosslinking reactions.

In some embodiments, the delivery of the irradiation is continuous. In some embodiments, the delivery of irradiation is pulsed. In some embodiments, the radiation is applied using a beam profile of greater than 12 mm at 10 mm from a surface of the tarsal plate. In some embodiments, a narrower radiation beam of, for example, about 11 mm, may be used if it is repositioned at time intervals, for example to ensure that the entire surface of the tarsal plate is irradiated.

In some embodiments, the tarsal plate is irradiated over its entire exposed surface. In some embodiments the tarsal plate is irradiated substantially where the photosensitizer has been applied.

In some preferred embodiments, an eye shield or protector, such as a metallic eye protector, is placed under the eyelid and against the anterior aspect of the eye globe prior to irradiation to protect the eye globe from radiation.

In some embodiments of the methods herein, irradiation is carried out in the presence of one or more crosslinking agents. A crosslinking agent will preferably be pharmaceutically acceptable. The skilled person will understand that a crosslinking agent will be preferably substantially non-irritant and non-toxic. In some embodiments irradiation is carried out in the presence of $O_2$ gas. In some embodiments a method is carried out in the presence of additional $O_2$ gas to provide $O_2$ concentrations greater than those present in the normal atmospheric conditions or in the tarsal tissue. In some embodiments, the additional $O_2$ is provided at the site of crosslinking during irradiation. In some embodiments $O_2$ gas is delivered to the surface of the tarsal plate in the proximity of the irradiation site, for example using a delivery device such as an applicator. In some embodiments, the $O_2$ gas is humidified prior to use. Methods of generating humidified $O_2$ gas are known to the skilled person, and include passing the gas flow through a humidifier prior to delivery to the required site.

In some embodiments, the methods herein comprise making an incision to expose the tarsal plate and subsequent closure of the incision after irradiation with the photo-activating radiation. Techniques for making incisions are well known in the art and include, for example, use of a scalpel or a laser. Techniques and materials for effecting closure of incisions are well known in the art, and include sutures, for example silk, catgut or synthetic sutures; adhesives, for example 2-octyl cyanoacrylate; adhesive tapes or strips; or staples.

In some embodiments, a method may be performed simultaneously or sequentially in combination with an additional tightening procedure, such as a surgical tightening procedure. Suitable surgical tightening procedures are well known in the art, and include for example full-thickness wedge excision; lateral tarsal strip; lateral canthal tendon plication; or lateral tarsorrhaphy.

In some embodiments there is provided a method of treating eyelid laxity in an individual comprising the steps of:

(a) making an incision line within an eyelid crease in an upper eyelid, and/or about 4 mm from the margin in a lower eyelid;
(b) anesthetizing the eyelid;
(c) sterilizing the eyelid;
(d) performing a horizontal skin incision on the eyelid on the marked incision line;
(e) deepening the incision through the underlying orbicularis oculi muscle down to the orbital septum;
(f) creating a pretarsal pocket in the central eyelid, extending medially and laterally;
(g) exposing the anterior aspect of the tarsal plate;
and either:
(h) instilling a photosensitizer solution into the pretarsal pocket; and
(i) removing the excess of solution after from 6-60 minutes;

or:
(j) as an alternative to step (h), inserting an absorbent material soaked in an aqueous solution of photosensitizer into the pretarsal pocket; and
(k) maintaining the absorbent material in the pretarsal pocket for from 6-60 minutes; and removing the absorbent material;
and then:
(l) inserting an eye protector under the eyelid and against the anterior aspect of the eye globe;
(m) applying directly to the exposed tarsal tissue a UV-A radiation beam, optionally in the presence of 02 gas delivered close to the irradiation site to effect cross-linking, for example for 1 to 60 minutes or 6 to 60 minutes, or 1 to 6 minutes, or 1 to 4 minutes, depending on the irradiance level;
(n) removing the corneal protector; and
(o) closing the skin incision on the eyelid.

In some embodiments there is provided a method of treating eyelid laxity in an individual comprising the steps of:
(a) making an incision line, suitably with an indelible skin marker, within an eyelid crease in an upper eyelid, and/or 4 mm from the margin in a lower eyelid;
(b) anaesthetizing the eyelid, for example by injecting local anesthetic into the eyelid via transcutaneous or transconjunctival delivery;
(c) sterilizing the eyelid skin, for example with Betadine, and placing a sterile drape to expose the individual's face;
(d) performing a horizontal skin incision on the eyelid on the marked line, for example using a scalpel;
(e) deepening the incision through the underlying orbicularis oculi muscle down to the orbital septum, for example using a hand-held hot-temperature cautery machine;
(f) creating with the hot-temperature cautery machine a pretarsal pocket in the central eyelid, extending medially and laterally;
(g) exposing the anterior aspect of the tarsal plate, preferably approximately 20×8 mm on the upper eyelid, or 20×3 mm on the lower eyelid, avoiding breach of the eyelid margin at the gray line, and dehiscence of the levator aponeurosis;
(h) placing a traction suture in the pretarsal skin, close to the incision line; and either:
(i) instilling a photosensitizer, for example an aqueous solution of riboflavin 5'-phosphate monosodium salt into the pretarsal pocket; and
(j) removing the excess of solution after, for example 6-60 minutes, using for example an absorbent material, such as a sponge;
or:
(k) as an alternative to step (i), inserting an absorbent material, such as a neurosurgical patty, soaked in an aqueous solution of photosensitizer, such as riboflavin 5'-phosphate monosodium salt, into the pretarsal pocket; and
(l) maintaining the absorbent material in the pretarsal pocket, for example for 6-60 minutes and removing the absorbent material;
and then:
(m) inserting a metallic eye protector under the eyelid and against the anterior aspect of the eye globe;
(n) exposing the tarsal plate, for example by clamping the traction suture to the drape, for example using an artery forcep;
(o) applying directly to the exposed tarsal tissue a radiation beam, for example UV-A, optionally in the presence of $O_2$ gas delivered close to the irradiation site, for example for 1 to 60 minutes, or 6 to 60 minutes or 1 to 6 minutes, or 1 to 4 minutes, depending on the irradiance level;
(p) removing the corneal protector and the traction suture;
(q) checking the eyelid position, both open and closed, to ensure the elevator palpebri or lower eyelid retractors are functioning normally;
(r) closing the incision on the eyelid, for example with a suture.

Figure 1B:
FIG. 1B is a representation of a horizontal skin incision on an upper eyelid.
Figure 2:
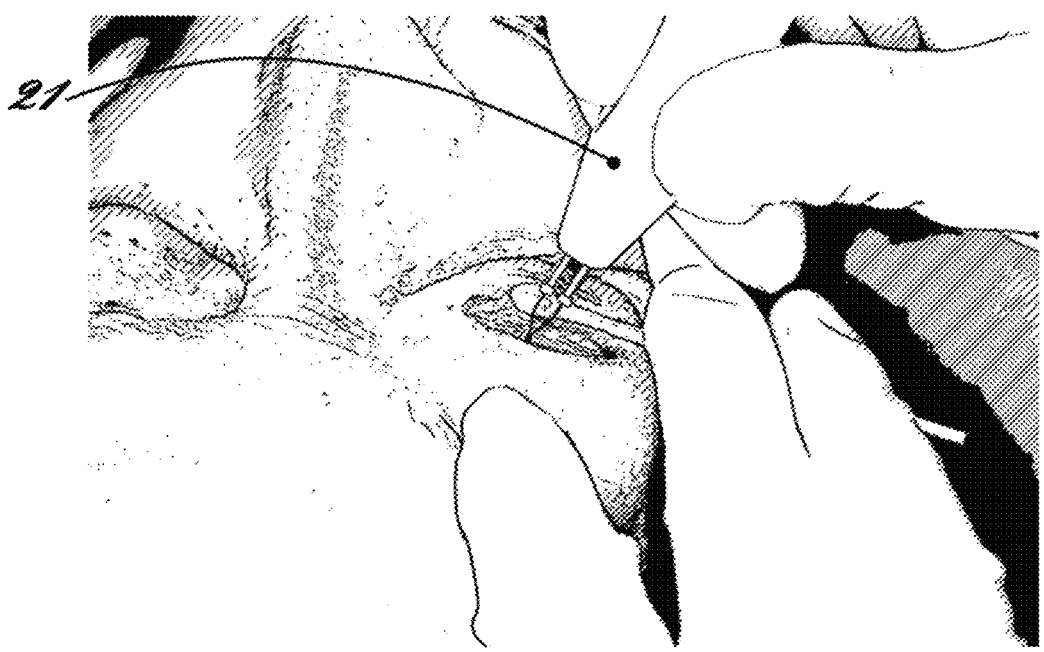
FIG. 2 shows cauterization made with a Bovie hot-temperature cautery machine through the underlying orbicularis oculi muscle down to the orbital septum.
Figure 3:
FIG. 3 shows the creation of a pretarsal pocket in the central upper eyelid using the Bovie cautery machine.
Figure 4:
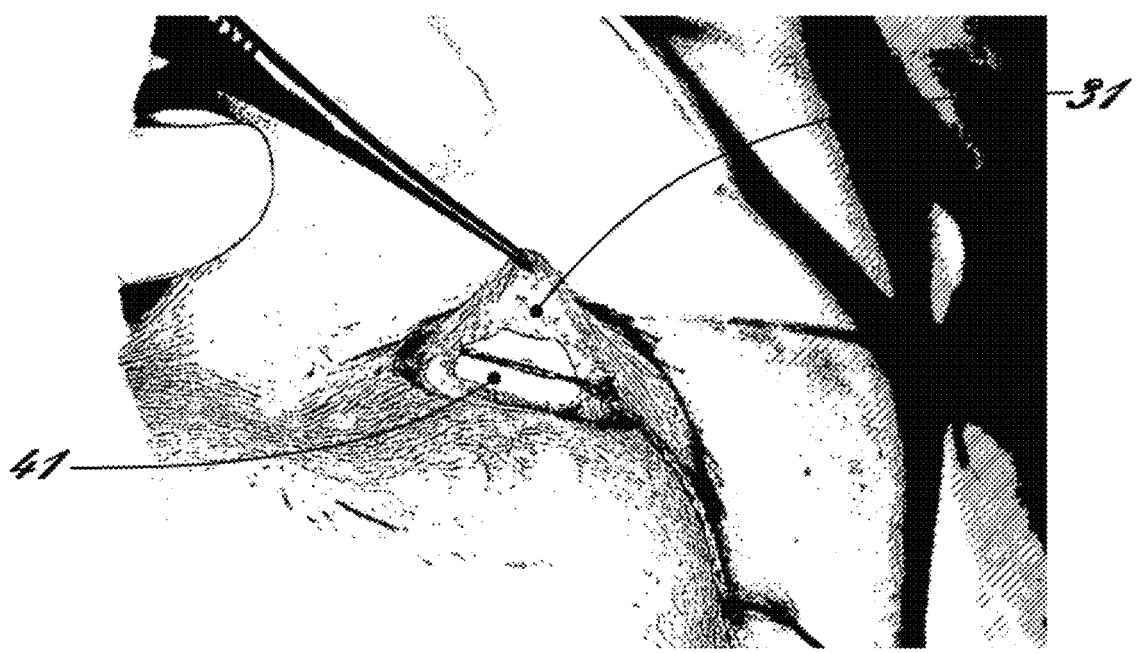
FIG. 4 shows the insertion of a neurosurgical patty, soaked in a photosensitizer solution, into the pretarsal pocket.
Figure 5:
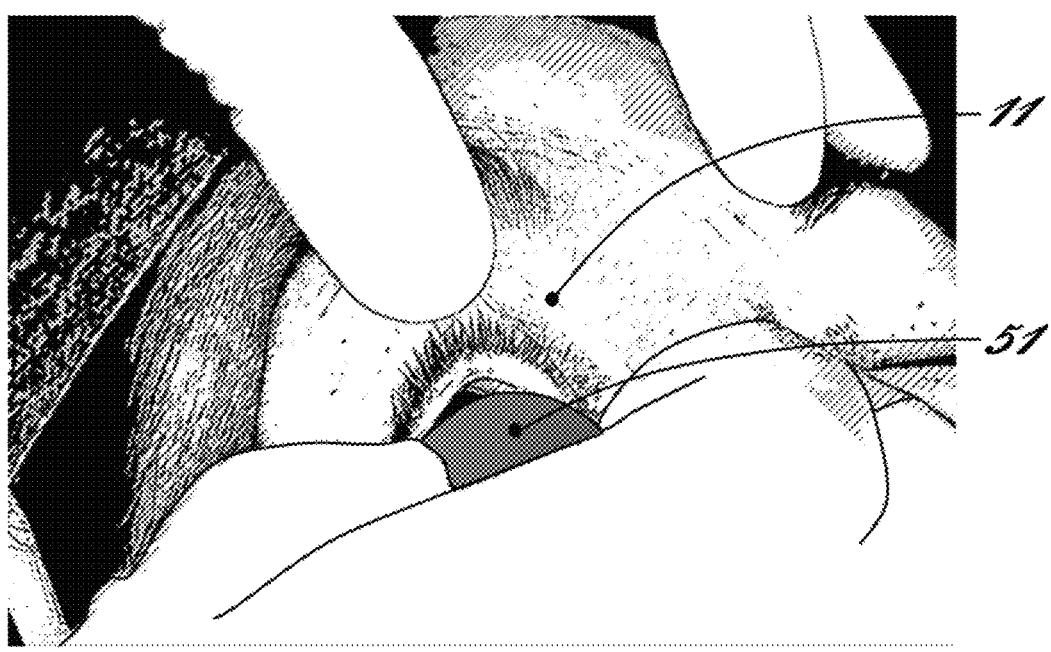
FIG. 5 shows the insertion of a corneal protector against the eye globe.
Figure 6:
FIG. 6 shows the exposure of the anterior aspect of the tarsal plate of the upper eyelid, where irradiation is delivered.
Figure 7:
FIG. 7 shows the closure of the incision using sutures.

An exemplary procedure in accordance with the methods herein is carried out in accordance with the method as illustrated in FIGS. 1 to 8. FIG. 1B depicts the upper eyelid 11 and the incision 12 on the upper eyelid. FIG. 2 depicts cauterization through the muscles made with a hand-held hot-temperature cautery machine, for example a Bovie cautery instrument 21 (Bovie Medical Corporation, Purchase, N.Y., 10577, USA). FIG. 3 depicts the creation of a pretarsal pocket 31 using the Bovie cautery tool 21. FIG. 4 depicts the insertion into the pretarsal pocket 31 of a neurosurgical patty 41 soaked in a photosensitizer solution. FIG. 5 depicts the insertion of a metallic eye protector 51 under the eyelid and against the anterior aspect of the eye globe. FIG. 6 depicts the clamping of a traction suture 62 to the drape 61 in order to expose the anterior aspect of the upper tarsal plate, where the irradiation is applied. FIG. 7 depicts the final closure of the incision 12 with suture 71.

In one embodiment the method for the treatment of an eye affected by eyelid laxity is performed as follows. Local anesthetic (e.g. Alcaine) is applied to the patient's eye. An incision line is marked with indelible skin marker, within the eyelid crease in the upper eyelid, or 4 mm from the margin in the lower eyelid. Local anesthetic (2.5-3 mL) is injected into the eyelid either transcutaneously or transconjuctivally. The skin is sterilized with a suitable preparation (e.g. half-strength Betadine™), and sterile drape is placed around surgical field, exposing the patient's face. A horizontal skin incision 12 is performed on the eyelid 11 on the marked line, using a blade #15 scalpel, as shown in FIG. 1B. As indicated in FIG. 2, the incision is extended through the underlying orbicularis oculi muscle down to the orbital septum using a hand-held hot-temperature cautery machine, e.g. a Bovie cautery tool 21. A pretarsal pocket 31 is created in the central eyelid, extending medially and laterally, as shown in FIG. 3. The anterior aspect of the tarsal plate is exposed, approximately 20×8 mm on the upper eyelid, or 20×3 mm on the lower eyelid. Care is taken not to breach the eyelid margin at the grey line, and to avoid dehiscence of the levator aponeurosis. A traction suture (for example using 6-0 Vicryl) is placed in the pretarsal skin, close to the incision line. Aqueous solution of the photosensitizer riboflavin 5'-phosphate monosodium salt (1 to 5 mL of 0.1 to 0.5% by weight) is instilled into the tarsal plate where it remains for from 6 to 60 minutes. Excess solution is removed by using a sponge device, e.g. a Weck-Cell™ cellulose eye spear sponge. Alternatively, as depicted in FIG. 4, a neurosurgical patty (25×12 mm) 41 trimmed to an appropriate size, is soaked for about 5 minutes in the aqueous solution of the photosensitizer, and then inserted into the pretarsal pocket 31, where it remains for from 6 to 60 minutes prior to removal. A metallic eye protector 51 is inserted under the eyelid 11 and against the anterior aspect of the eye globe, as shown in FIG. 5. The traction suture 62 is clamped to drape 61 with an artery forcep, as shown in FIG. 6, in order to expose the tarsal plate and allow direct irradiation of the tarsal tissue by a UV-A radiation beam. The UV-A radiation may be provided by a commercially available UV corneal crosslinking machine. The duration of the irradiation will depend on the wavelength and power of the radiation beam, and can be readily determined by the skilled person. Typical irradiation times at an irradiance of 3 mW/cm$^2$ are 6 to 60 minutes, suitably from 10 to 50 minutes, 15 to 45 minutes, 20 to 40 minutes, 30 to 40 minutes, 20 to 30 minutes or approximately 30 minutes. Typical irradiation times at an irradiance of 6 mW/cm$^2$ are 6 to 60 minutes, suitably from 10 to 40 minutes, 15 to 45 minutes, 20 to 40 minutes, 20 to 30 minutes, 15 to 20 minutes or approximately 30 minutes. Humidified $O_2$ gas can be delivered at the site of crosslinking if desired. After the radiation treatment, the corneal protector and traction suture are removed. The eyelid position is checked, in both opened and closed situations, to ensure that the elevator palpebri or lower eyelid retractors are functioning normally. If necessary, reattachment is performed surgically. The skin incision 12 on the eyelid 11 is then closed with the suture 71 (e.g. 6-0 Vicryl, Ethicon Inc.), as shown in FIG. 7.

3. Systems and Apparatus

There is further advantageously provided a system 100 (FIG. 1A) for crosslinking tarsal plate tissue comprising:
an applicator 110 that applies or delivers a photosensitizer 120 to an exposed tarsal plate of an eye; and
   a radiation source 130 for providing photo-activating radiation to the tarsal plate.

In another aspect there is provided a kit or commercial package for crosslinking tarsal plate tissue comprising:
an applicator that applies or delivers a photosensitizer to an exposed tarsal plate of an eye; and
a radiation source for providing photo-activating radiation to the tarsal plate; together with instructions to treat eyelid laxity or crosslink a tarsal plate.

In yet another aspect there is provided a kit or commercial package for crosslinking tarsal plate tissue comprising:
an applicator that applies or delivers a photosensitizer to an exposed tarsal plate of an eye; and
a radiation source for providing photo-activating radiation to the tarsal plate wherein the beam width is greater than 12 mm at 10 mm from a surface of the tarsal plate; and, optionally, instructions to treat eyelid laxity or crosslink a tarsal plate.

In preferred embodiments, the radiation source provides a beam profile of greater than 12 mm at a distance of 10 mm from a surface of the tarsal plate, preferably the beam profile is from 13 mm to 15 mm at a distance of 10 mm from a surface of the tarsal plate.

Radiation sources are known in the art, and suitable sources are commercially available. In some embodiments the radiation is UV-A with a wavelength of from 320 to 400 nm. Radiation sources include those suitable for or intended for corneal crosslinking procedures such as, for example, XLink™ (Optos, Dunfermline, Scotland); CBM Vega XLink Crosslinking System (Carleton Optical, Chesham, UK); LightLink CXL™ (LightMed, San Clemente, Calif., USA); UV-X™ 2000 Crosslinking System (IROC Innocross, Zurich, Switzerland) and KXL™ CrossLinking System (Avedro Waltham, Mass., USA). These radiation sources typically have a beam width of approximately 10 to 12 mm, or about 11 mm. The skilled person would understand that repositioning of such a radiation beam would be necessary to effect radiation of the entire surface of an exposed tarsal plate. Alternatively, the radiation source instrument may be modified to produce a greater beamwidth to irradiate substantially all of the tarsal plate surface at the same time.

Applicators for delivering or applying a photosensitizer to an exposed tarsal plate of an eye include syringes, droppers, vials, ampoules, pipettes, and absorbent materials such as surgical sponges and neurosurgical patties. In some embodiments a preferred applicator is an absorbent material, such as a neurosurgical patty. The skilled person will appreciate that absorbent materials may be cut or folded to size where necessary.

A system, kit or commercial package as defined herein may also comprise a photosensitizer or a photosensitizer composition as defined herein.

The system, kit or commercial package may also comprise a delivery device 140 that delivers $O_2$ gas to the exposed tarsal plate. In some embodiments the $O_2$ gas may be delivered using a nozzle, syringe, diffuser, or the like. Suitable methods of delivering $O_2$ to the exposed tarsal tissue and/or the site of irradiation or site of crosslinking are disclosed in, for example, U.S. Pat. No. 8,574,277.

4. Compositions

Photosensitizers suitable for use in the methods described herein are molecules having a chemical structure which includes a chromophore that absorbs radiation at a wavelength of the photo-activating radiation. The photosensitizer, on irradiation by photo-activating irradiation, produces a chemical change in another molecule, for example, $O_2$ and/or one or more tissue molecules, for example collagen molecules. This can initiate crosslinking thus producing chemical change in the tissue. In some embodiments the methods defined herein generate crosslinking in collagen. Preferably the photosensitizers are non-irritant, and pharmaceutically acceptable. A photosensitizer may be in the form of a pharmaceutically acceptable salt, derivative or solvate thereof. Preferably a photosensitizer is soluble to a sufficient extent in an aqueous carrier to provide a concentration of from 0.1% to 10% w/v, preferably 0.1% to 5% w/v, 0.1% to 2% w/v, 0.1% to 1% w/v, 0.1% to 0.5% w/v, or 0.1% to 0.3% w/v. Suitable photosensitizers are known in the art, and are commercially available from, for example Sigma Aldrich Co. LLC. A preferred photosensitizer is riboflavin as an aqueous soluble form, for example a sodium salt of riboflavin 5'-phosphate, or a pharmaceutically acceptable solvate thereof. Suitable photosensitizers are known in the art, and are commercially available from, for example Sigma Aldrich Co. LLC).

Photosensitizer compositions used in the methods and systems defined herein are preferably pharmaceutical compositions and may be formulated and administered using methods known in the art. Techniques for formulation and administration may be found in, for example, *Remington: The Science and Practice of Pharmacy*, Loyd V. Allen, Jr (Ed), The Pharmaceutical Press, London, 22$^{nd}$ Edition, September 2012.

A photosensitizer composition is preferably in a form suitable for topical administration to the tarsal plate. In some embodiments, the photosensitizer composition is formulated for example as an emulsion, cream, lotion, gel, jelly, paste, ointment, solution, salve, or solution, especially as a gel, oil in water emulsion or solution, as described in, for example, the United States Food and Drug Administration Monograph No. C-DRG-00201 entitled *CDER Data Standards Manual Definitions for Topical Dosage Forms*. In some embodiments, the composition is a solution.

Preferably the photosensitizer is in a solubilized form. Suitably, a photosensitizer pharmaceutical composition is in a sterile aqueous solution. In some embodiments the sensitizer is formulated in a sterile ophthalmic solution. Suitably a sterile aqueous photosensitizer solution is packaged in a vial, ampoule, syringe, for example as a single use syringe.

Aqueous compositions, such as solutions, of a photosensitizer, for example a water soluble form of riboflavin, are commercially available or may be prepared using known methods. For example, a water soluble salt, derivative or solvate of riboflavin may be dissolved in an aqueous pharmaceutically acceptable carrier selected from, but not limited to, saline, water, aqueous buffer, an aqueous solution comprising water and a miscible solvent, and combinations thereof. An aqueous composition may additionally include pharmaceutically acceptable excipients selected from viscosity modifiers such as dextran, buffers, rheology modifiers, surfactants, and chelating agents.

Commercially available riboflavin solutions include VibeX Xtra™, [0.22% riboflavin, saline isotonic]; MedioCROSS TE [0.25% riboflavin 5'-phosphate, 1.2% HPMC (hydroxypropylmethylcellulose), 0.01% BAC (benzalkonium chloride)]; MedioCROSS M [0.1% riboflavin 5'-phosphate, 1.1% HPMC]; VibeX Rapid™, [0.1% riboflavin 5'-phosphate, saline, HPMC]; ParaCel™ [0.25% riboflavin 5'-phosphate, HPMC, BAC], Photrexa [0.146% riboflavin 5'-phosphate ophthalmic solution] or Photrexa viscous [0.146% riboflavin 5'-phosphate in 20% dextran ophthalmic solution], all available from Avedro Inc, USA. Riboflavin is typically in the form of riboflavin 5'-phosphate sodium salt.

Materials for use in surgical procedures are well known to the skilled person and are readily available from commercial sources. Suitable local anaesthetics for anaesthetizing the eyelid are well known to the skilled person and include, for example Alcaine® (Proparacaine hydrochloride), Naropin® (Ropivicane hydrochloride), Marcaine™ (Bupivacaine hydrochloride) and Novesin® (Benoxinate, Oxybuprocaine hydrochloride). Suitable antiseptics include Betadine® (povidone/iodine) and Betasept® (chlorhexidine). Wound closure may be effected using techniques known in the art and include sutures; adhesives; adhesive tapes; staples and the like.

In order that the methods, compositions and apparatuses may be readily understood and put into practical effect, particular preferred embodiments will now be described by way of the following non-limiting examples.

EXAMPLES

Materials and Methods

The experiments described were performed on tarsal plates excised from sheep, based on the fact that the ovine and human tarsal plates are structurally and functionally identical, as shown in: M. J. Boileau, M. A. Gilmour: "Diseases of the eye", in Sheep and Goat Medicine, 2nd Edn, D. G. Pugh, A. N. Baird (Eds), Elsevier, Amsterdam, 2012, pp. 406-410; D. A. Samuelson: "Ophthalmic structures", in *Essentials of Veterinary Ophthalmology*, 3rd Edn, K. N. Gelatt (Ed.), Wiley, Oxford, U K, 2014, pp. 12-20.

Riboflavin and its salts, solvates and derivatives are readily available from commercial sources. For example USP riboflavin 5'-phosphate monosodium salt is commercially available from Sigma-Aldrich Co LLC. Aqueous 0.25% riboflavin is commercially available as ParaCel™ from Avedro Inc, USA. Aqueous 0.1% riboflavin 5'-phosphate (dextran free) is available from Avedro Inc, USA as VibeX Rapid™.

Commercially available corneal crosslinking systems are available, for example, Opto XLink™ corneal crosslinking system (Opto Electrônica S/A, São Carlos,-SP 13563-330, Brazil; Opto USA Corp, North Miami, Fla.-33181, USA; opto.com.br); or KXL Accelerated Cross-Linking System (Avedro, Inc, Waltham, Mass. 02451, USA; avedro.com). Alternatively, the UV curing system OmniCure® 1500 (Excelitas Technologies Corp, Waltham, Mass., 02451; excelitas.com) can be used to provide a large range of irradiances.

Example 1

Crosslinking of Sheep Tarsal Plates

Upper and lower eyelids were isolated from cadaveric sheep eyes (1-2 years old), and the tarsal plates were excised. The resulting tarsal strips, with a mean thickness of 1.5±0.2 mm for both upper and lower eyelids, were treated with a commercially available riboflavin solution (ParaCel™) for 30 min, and then irradiated in a commercially available corneal crosslinking system (Opto XLink™) with UV-A radiation (365 nm) at an irradiance of either 3 mW/cm$^2$ or 6 mW/cm$^2$, for various durations. Humidified $O_2$ gas was delivered at the site of crosslinking.

Example 2

Tensile Measurements on Sheep Tarsal Plates

Tensile measurements on either untreated and crosslinked tarsal strips were performed in an Instron mechanical microtester equipped with a 50-N load cell, at a set gauge distance of 6 mm and a speed of 1.5 mm/min. The stress-strain plots were recorded and Young's moduli were computed in the linear region. Four to six measurements for each specimen were performed and recorded. The results were statistically processed by the one-way analysis of variance (ANOVA) in conjunction with Tukey-Kramer multiple comparisons, using the GraphPad® Prism software (Version 6.0).

Example 3

Stress-Strain Plots of the Sheep Tarsal Plates

Figure 8:
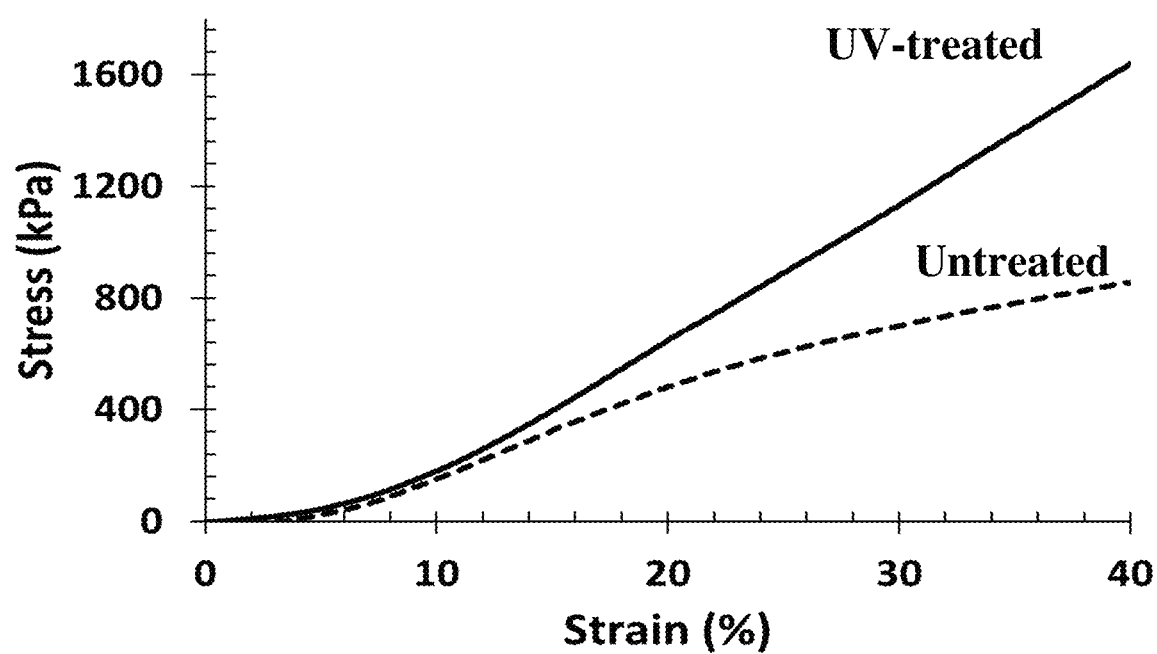
FIG. 8 shows the stress-strain plots for untreated and UV-crosslinked (365 nm, 6 mW/cm$^2$) sheep tarsal plates.

FIG. 8 shows the stress-strain plots of an untreated tarsal plate and a UV-crosslinked tarsal plate, demonstrating the effect of the crosslinking process on the mechanical properties of the tarsal fibrocartilage tissue.

Example 4

Mechanical Properties of Sheep Tarsal Plates

Table 1 presents the UV-irradiation conditions, and the values of Young's modulus and stress at 20% strain for the sheep tarsal strips isolated from the upper and lower eyelids. The crosslinking process increased the stiffness of the tarsal tissue, as indicated by the higher values of Young's modulus and stress.

TABLE 1

Young's modulus and stress values at 20% strain measured for the sheep tarsal plates excised from upper and lower lids

| Tarsus location | UV Conditions Irradiance (mW/cm$^2$) | Time (minutes) | n | Young's modulus (MPa) | Increase in Young's modulus (%) | Stress (kPa) |
|---|---|---|---|---|---|---|
| Upper eyelid | Untreated | — | 6 | 3.1 ± 1.5 | — | 319.6 ± 224.6 |
| | 3 | 30 | 4 | 3.9 ± 0.6 | 25.8 | 449.6 ± 104.3 |
| | 6 | 30 | 4 | 4.8 ± 1.1 | 54.8 | 480.1 ± 121.4 |
| Lower eyelid | Untreated | — | 6 | 4.2 ± 1.8 | — | 459.6 ± 212.9 |
| | 3 | 30 | 4 | 5.0 ± 1.4 | 19.0 | 685.6 ± 327.2 |
| | 6 | 30 | 4 | 5.5 ± 0.8 | 31.0 | 477.6 ± 163.2 |

Example 5

Crosslinking of the Sheep Tarsal Plates at High Irradiance

Upper and lower eyelid tarsal strips excised from cadaveric sheep eyes were crosslinked at high irradiance in a KXL Accelerated Cross-Linking System machine, which delivered a maximum irradiance of 45 mW/cm$^2$ at the maximum fluence of 7.2 J/cm$^2$. The tarsal specimens were immersed in 0.1% riboflavin solution (VibeX Rapid™) for 30 min, and then irradiated continuously with radiation UV-A (365 nm) without delivery of O$_2$ gas at the site of crosslinking. The irradiance levels of 150 mW/cm$^2$ and 250 mW/cm$^2$, respectively, were generated using the UV curing system OmniCure® 1500, equipped with a 365-nm filter.

Table 2 presents the conditions used for crosslinking at high irradiances.

TABLE 2

Conditions for crosslinking at high irradiances

| Irradiance (mW/cm$^2$) | Fluence (J/cm$^2$) | Time (s) | Number of samples (n) | |
|---|---|---|---|---|
| | | | Upper eyelid | Lower eyelid |
| 30 | 5.4 | 180 | 2 | 2 |
| 45 | 5.4 | 120 | 3 | 3 |
| 45 | 7.2 | 160 | 3 | 3 |
| 150 | 27.0 | 180 | 3 | 5 |
| 250 | 45.0 | 180 | 3 | 5 |

Figure 9:
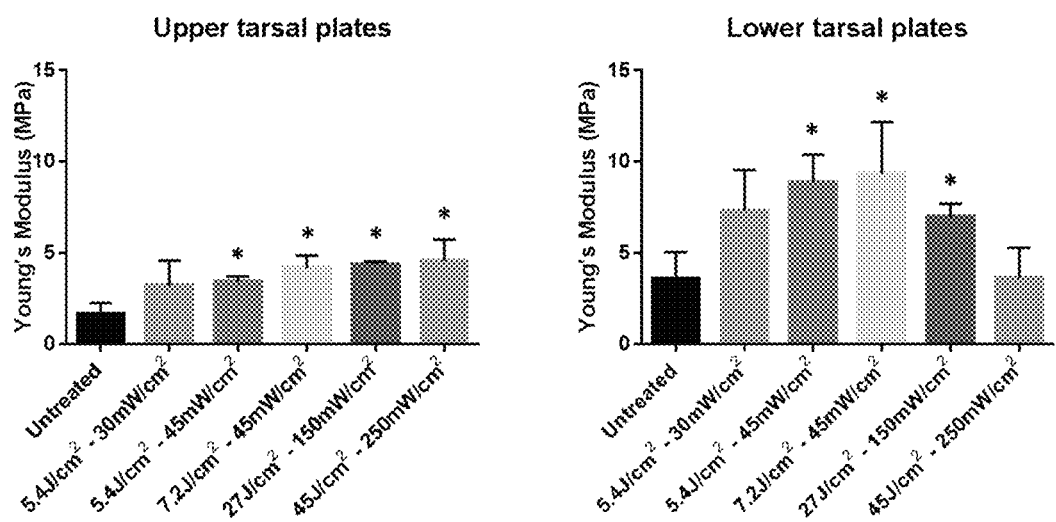
FIG. 9 shows comparative bar graphs of the experimentally measured Young's moduli, prior and after crosslinking with UV-A radiation at high irradiances of the sheep tarsal tissue from upper and lower eyelids. The asterisk indicates statistical significance.
Figure 10:
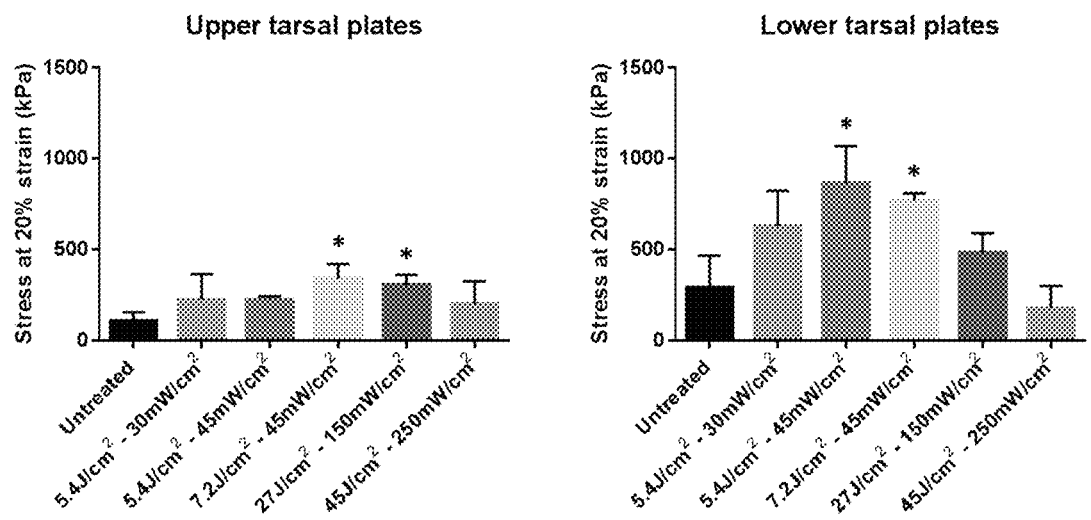
FIG. 10 shows comparative bar graphs of the experimentally measured stress at 20% strain, prior and after crosslinking with UV-A radiation at high irradiances of the sheep tarsal tissue from upper and lower eyelids. An asterisk indicates statistical significance.

FIGS. 9 and 10 show, respectively, the effect of irradiation at high irradiances on Young's modulus (stiffness) and on tensile stress (mechanical strength) of the tarsal tissue specimens excised from upper and lower eyelids of sheep eyes. The process of crosslinking increased significantly the rigidity of the tarsal fibrocartilage tissue. However, at irradiance levels exceeding 150 mW/cm$^2$, the increase in stiffness or strength of the tarsal tissue appears to cease as an opposite effect, potentially due to photodegradation, becomes evident leading to the decline of these properties.

Example 6

Effect of Different Procedures for the Application of Photosensitizer Solution

Figure 11:
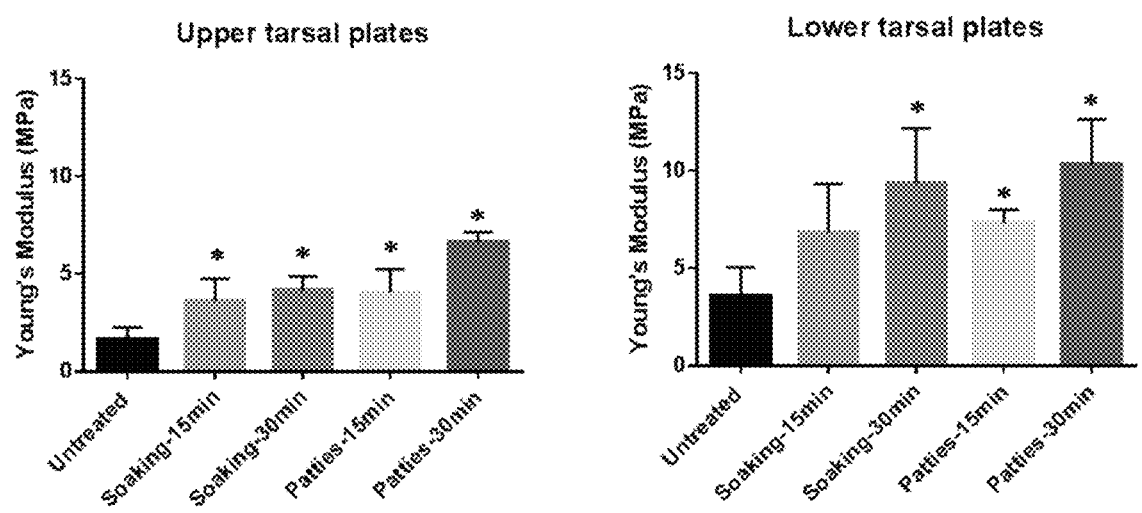
FIG. 11 shows comparative bar graphs of the experimentally measured Young's moduli, prior and after crosslinking of the sheep tarsal tissue from upper and lower eyelids with UV-A radiation at an irradiance of 45 mW/cm$^2$, with the photosensitizer solution being applied either by direct immersion or through contact with fluid-saturated surgical patties. An asterisk indicates statistical significance.
Figure 12:
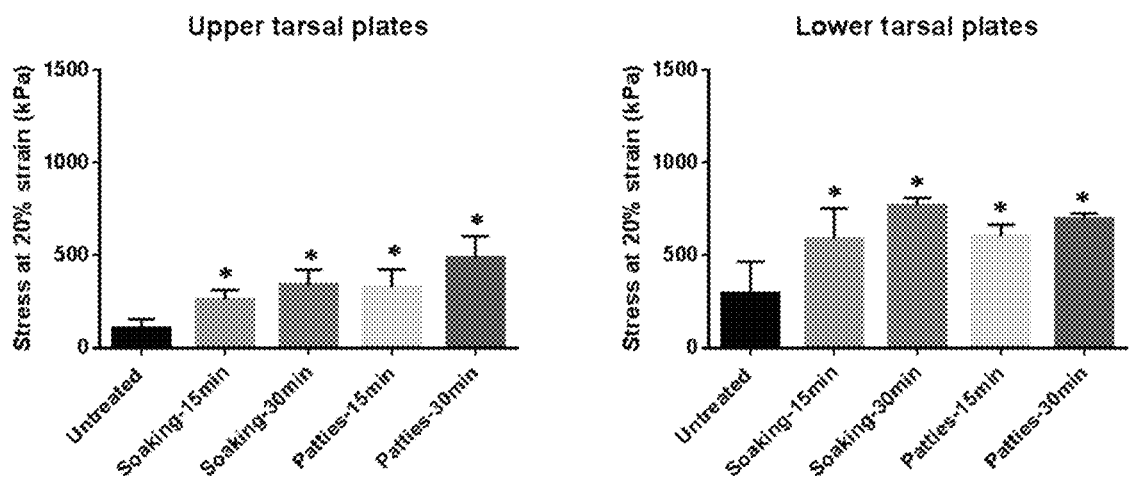
FIG. 12 shows comparative bar graphs of the experimentally measured stress at 20% strain, prior and after crosslinking of the sheep tarsal tissue from upper and lower eyelids with UV-A radiation at an irradiance of 45 mW/cm$^2$, with the photosensitizer solution being applied either by direct immersion or through contact with fluid-saturated surgical patties. An asterisk indicates statistical significance.

Two different approaches were used for treating with 0.1% riboflavin solution (VibeX Rapid™) the ovine upper and lower eyelid tarsal strips prior to their irradiation. In the first procedure, the strips were soaked in the riboflavin solution for two different durations (15 min or 30 min), and then irradiated. In the second procedure, the strips were kept in contact with surgical patties that were completely soaked in riboflavin solution. The contact between the tarsal strips and patties was maintained for 15 min or 30 min. Following the riboflavin treatment, the samples were irradiated using the OmniCure® 1500 machine, which delivered a maximum irradiance of 45 mW/cm$^2$ at the maximum fluence of 7.2 J/cm$^2$. The results presented in FIGS. 11 and 12 indicate that the mechanical properties were enhanced when the photosensitizer solution was applied to the tarsal tissue through an absorbent material such as a surgical patty.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the methods, compositions and apparatuses without limiting to any one embodiment or specific collection of features. Those of skill in the art will therefore appreciate that, in light of the instant disclosure, various modifications and changes can be made in the particular embodiments exemplified without departing from the scope of the methods, compositions and apparatuses defined herein. All such modifications and changes are intended to be included within the scope of the appended claims.

What is claimed is:

1. A method of treating eyelid laxity in a subject comprising:
    exposing a tarsal plate of an eye;
    applying, to at least part of the exposed tarsal plate, a photosensitizer that initiates crosslinking in response to photo-activating radiation; and
    irradiating the exposed tarsal plate with photo-activating radiation to initiate crosslinking in the tarsal plate tissue.

2. The method according to claim 1 wherein the photosensitizer is in solubilized form.

3. The method according to claim 1 wherein the photosensitizer is riboflavin or a pharmaceutically acceptable salt, derivative or solvate thereof.

4. The method according to claim 1 wherein the photosensitizer is riboflavin 5'-phosphate or a pharmaceutically acceptable salt or solvate thereof.

5. The method according to claim 1 wherein the photo-activating radiation is UV-A radiation.

6. The method according to claim 1 wherein the method comprises:
- exposing a tarsal plate of an eye by making an incision;
- applying, to at least part of the exposed tarsal plate, riboflavin or a pharmaceutically acceptable salt, derivative or solvate thereof in solubilized form;
- irradiating the exposed tarsal plate with UV-A radiation to initiate crosslinking in the tarsal plate tissue; and
- closing the incision.

7. The method according to claim 1 wherein the method further includes delivery of O2 gas at a site of irradiation.

8. The method according to claim 1 performed either simultaneously or sequentially in combination with an additional tightening procedure.

9. A method of crosslinking a tissue of a tarsal plate, the method comprising topical application, to the tarsal plate, of a photosensitizer that initiates crosslinking in response to photo-activating radiation and, simultaneously or subsequently, treating the tarsal plate with photo-activating radiation.

10. The method according to claim 9, wherein the photosensitizer is a pharmaceutical composition comprising riboflavin or a pharmaceutically acceptable derivative, salt or solvate thereof.

11. The method according to claim 10, wherein the pharmaceutical composition comprises an aqueous solution of riboflavin 5'-phosphate or a pharmaceutically acceptable salt or solvate thereof.

12. The method according to claim 9, wherein the photo-activating radiation is UV-A radiation.

* * * * *